United States Patent [19]

Scherrer

[11] 4,174,403

[45] Nov. 13, 1979

[54] 5,6-METHYLENEDIOXY-2-NITRO-3-PHENYLBENZOFURANS

[75] Inventor: Robert A. Scherrer, White Bear Lake, Minn.

[73] Assignee: Riker Laboratories, Inc., Northridge, Calif.

[21] Appl. No.: 919,415

[22] Filed: Jun. 26, 1978

[51] Int. Cl.² ............................................. A61K 31/36
[52] U.S. Cl. ............................... 424/282; 260/340.5 R
[58] Field of Search ................... 260/340.5 R; 424/282

[56] References Cited

U.S. PATENT DOCUMENTS 3,485,835  12/1969  Brandstrom et al. ......... 260/340.5 R
4,048,323  9/1977  Scherrer ........................... 424/285
4,066,782  1/1978  Scherrer ........................... 424/285
4,067,993  1/1978  Scherrer ........................... 424/285

FOREIGN PATENT DOCUMENTS 846502  3/1977  Belgium .
2642877  4/1977  Fed. Rep. of Germany .

Primary Examiner—Ethel G. Love
Attorney, Agent, or Firm—Cruzan Alexander; Donald M. Sell; Donald C. Gipple

[57] ABSTRACT

5,6-Methylenedioxy-2-nitro-3-phenylbenzofurans, optionally substituted on the 3-phenyl group, which are active as antimicrobial agents, processes for their use and intermediates therefor.

7 Claims, No Drawings

5,6-METHYLENEDIOXY-2-NITRO-3-PHENYL-BENZOFURANS

BACKGROUND OF THE INVENTION

This invention relates to a class of compounds wherein 5,6-methylenedioxy-2-nitro-3-phenylbenzofuran is optionally substituted on the 3-phenyl ring by halogen, methyl or methoxy, to the use of these compounds as antimicrobial agents and to intermediates useful in their synthesis.

Certain 2-nitro-3-phenylbenzofurans have been reported to be active antimicrobial agents (e.g. see U.S. Pat. No. 4,048,323; 4,066,782 and 4,067,993; Belgian Patent 846,502 and German Offenlegungschrift P 2,642,877). However, none of the known compounds have the 5,6-methylenedioxy substitution of the compounds of the invention, and, in fact, no 5,6-methylenedioxybenzofurans whatsoever (with or without 2-nitro and/or 3-phenyl substitution) have been disclosed heretofore.

DETAILED DESCRIPTION OF THE INVENTION

The present invention relates to 5,6-methylenedioxy-2-nitro-3-phenylbenzofurans which are optionally substituted on the 3-phenyl group. It also relates to the use of the compounds as antimicrobial agents and to synthetic intermediates useful for the preparation of the compounds of the invention.

According to the present invention, there is provided a class of compounds of the formula wherein X is hydrogen, halogen, methyl or methoxy. Halogen herein signifies fluorine, chlorine and bromine.

The pure compounds of the invention are generally white or yellow crystalline or amorphous solids. They are substantially insoluble in water and aliphatic hydrocarbons and are more soluble in acetone, lower alkanols, N,N-dimethylformamide and the like.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents.

The compounds of the invention are prepared from known starting materials (3,4-methylenedioxyphenol and unsubstituted or substituted α-bromoacetophenones as indicated) according to the following reaction scheme:

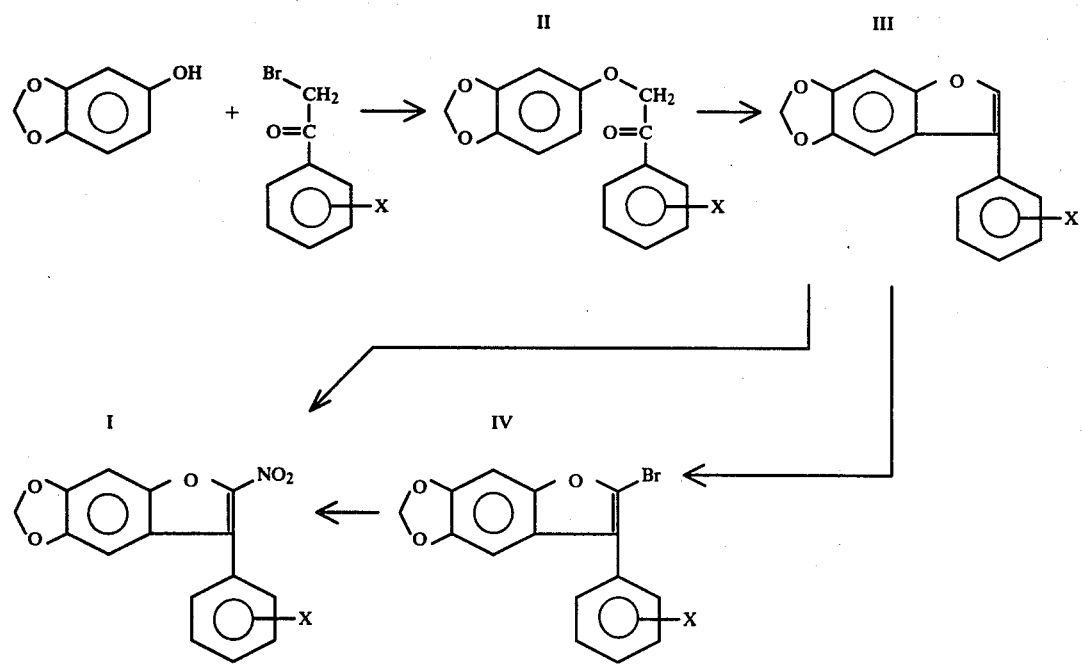

wherein X is as previously indicated.

The reaction to prepare the intermediate condensation products of formula II is generally carried out at a temperature from about 50° C. to the reflux temperature of the reaction mixture in an inert solvent such as benzene, glyme, tetrahydrofuran, ethanol, pyridine and the like and in the presence of a weak base, preferably an inorganic base such as an alkali metal carbonate, for example, sodium or potassium carbonate. The intermediate product (II) may then be obtained by such methods as extraction or chromatography.

The condensates II are cyclized by heating in the presence of polyphosphoric acid to form the compounds III which are easily separated by dilution of the reaction mixture with water and filtration or extraction. The compounds III are, in turn, brominated in the two position e.g. using bromine water or preferably bromine in a solvent such as dichloromethane, carbon tetrachloride or acetic acid. Alternatively the intermediates of formula III may be nitrated directly to provide the final product compounds of the invention of formula I. The direct nitration of the compounds III is carried out readily using methods similar to those described in several recent patents (for example U.S. Pat. Nos. 4,022,908; 4,013,692; 3,920,828) e.g. using dinitrogen tetraoxide in acetic acid. Intermediates of formula IV are reacted to replace the 2-bromo group with a nitro group using methods similar to those also described in several recent patents (for example, U.S. Pat. No. 4,022,908).

The intermediates II, III and IV are all novel classes of compounds and constitute additional aspects of the invention.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162-164, 1944, and Davis, B. D., and Mingioli, E. S., J. Bac. 66:129-136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli, Streptococcus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes, and broad spectrum activity can be predicted as a result of activity against them. All of the compounds of the invention possess antimicrobial activity towards one or more of the above microorganisms. The compounds maintain high activity against the microorganisms either in the absence or presence of 10 percent horse serum.

The invivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18-22 g., are infected intraperitoneally with the test culture. Treatment consists of three oral injections one, six and 24 hours after infrection. All mice are observed for extended periods, e.g. for two weeks, and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for treatment of a microbial infection will be an effective amount less than a toxic amount. The amount to be administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids or antibacterial agents, or to combine more than one compound described herein in a single composition.

Certain of the compounds are also active antiparasitics as shown by activity in laboratory tests versus the protozoan *Trichomonas sp.* In view of the outstanding antimicrobial activity of the compounds, they would also be expected to be effective growth promoters in various animal and bird species.

The following examples are given for the purpose of illustrating some of the synthetic methods useful in the invention, but are not intended to limit the invention. The melting points are uncorrected and the temperatures are in degrees Centigrade.

EXAMPLE 1

A mixture of 25 g. (0.181 mole) of 3,4-methylenedioxyphenol, 36 g. (0.181 mole) of α-bromoacetophenone and 41.2 g. (0.40 mole) of sodium carbonate in 350 ml. of benzene is heated to its reflux temperature and maintained at reflux for 16 hours. To the mixture is added 50 g. of potassium carbonate, and the mixture is refluxed for an additional 7 days while collecting water in a Barrett water trap. The mixture is then diluted with a mixture of water and benzene. The benzene layer is washed with water, then cold 5 percent sodium hydroxide solution. A precipitate forms in the benzene layer. It is collected, rinsed with benzene and dried to provide a white powder which is recrystallized from ethanol to provide α-(3,4-methylenedioxyphenoxy)acetophenone, m.p. 123°-126° C.

EXAMPLE 2

To a stirred portion of 50 g. of polyphosphoric acid at a temperature of 55° C. is added 50 g. (0.020 mole) of α-(3,4-methylenedioxyphenoxy)acetophenone. After one hour, the mixture is poured into cold water to provide a residue. The residue is collected and washed with water, then dissolved in dichloromethane. The dichloromethane solution is washed with water and saturated sodium chloride solution, then dried and concentrated. The solid residue is 5,6-methylenedioxy-3-phenylbenzofuran, m.p. 68°–75° C. The structural assignment is confirmed by infrared and nuclear magnetic resonance spectral analysis. It is used for further reaction without purification.

EXAMPLE 3

To a solution of 4.2 g. (0.018 mole) of 5,6-methylenedioxy-3-phenylbenzofuran in 80 ml. of dichloromethane is added 3.4 g. (0.04 mole) of sodium acetate, then 2.3 g. (0.018 mole) of bromine diluted with 20 ml. of dichloromethane is added dropwise to the solution. After stirring for one hour the mixture is washed with water and saturated sodium chloride solution, then dried. The dried solution is concentrated to dryness to provide a white powder which is found by nuclear magnetic resonance and infrared spectral analysis to be the desired product, 2-bromo-5,6-methylenedioxy-3-phenylbenzofuran, m.p. 109°–117° C.

EXAMPLE 4

To a solution of 5.2 g. (0.016 mole) of 2-bromo-5,6-methylenedioxy-3-phenylbenzofuran in 225 ml. of acetic acid is added with stirring 5.0 g. (0.024 mole) of cyclohexene-4-carboxylic acid, then 2.2 g. (0.024 mole) of dinitrogen tetraoxide in 25 ml. of acetic acid. After about one hour the mixture is poured into cold water, and the yellow product is collected and washed with water. The product is dissolved in dichloromethane, and the solution is washed with cold 5 percent sodium hydroxide solution, water and saturated sodium chloride solution, then dried. The solution is concentrated to dryness to provide a yellow residue which is recrystallized from a benzene-hexane mixture, then from an isopropanol-benzene mixture to provide yellow needles of 5,6-methylenedioxy-2-nitro-3-phenylbenzofuran, m.p. 180°–183° C.

| Analysis: | % C | % H | % N |
|---|---|---|---|
| Calculated for $C_{15}H_9O_5N$: | 63.6; | 3.2; | 5.0 |
| Found: | 63.6; | 3.4; | 5.0. |

Using the methods illustrated in Examples 1 to 4, the following compounds of the invention are prepared.

TABLE I

| Example No. | Starting Acetophenone | Final Product |
|---|---|---|
| 5 | CH₃O-C₆H₄-C(O)-CH₂Br | 5,6-methylenedioxy-2-nitro-3-(4-methoxyphenyl)benzofuran |
| 6 | H₃C-C₆H₄-C(O)-CH₂Br | 5,6-methylenedioxy-2-nitro-3-(3-methylphenyl)benzofuran |
| 7 | Br-C₆H₄-C(O)-CH₂Br | 5,6-methylenedioxy-2-nitro-3-(4-bromophenyl)benzofuran |
| 8 | F-C₆H₄-C(O)-CH₂Br | 5,6-methylenedioxy-2-nitro-3-(4-fluorophenyl)benzofuran |

What is claimed is:

1. A compound of the formula

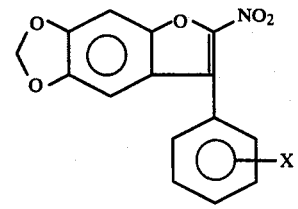

wherein X is hydrogen, halogen, methyl or methoxy.

2. The compound 5,6-methylenedioxy-2-nitro-3-phenylbenzofuran according to claim 1.

3. A method for arresting or inhibiting the growth of microorganisms comprising contacting microorganisms with a compound according to claim 1 in an amount sufficient to inhibit the growth of said microorganisms.

4. A compound of the formula

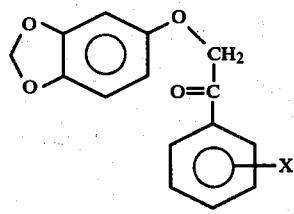

wherein X is hydrogen, halogen, methyl or methoxy.

5. A compound of the formula

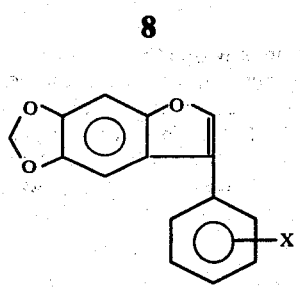

wherein X is hydrogen, halogen, methyl or methoxy.

6. A compound of the formula

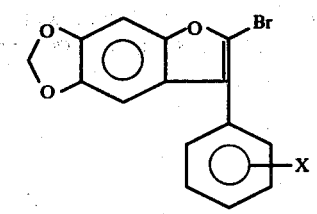

wherein X is hydrogen, halogen, methyl or methoxy.

7. A method for arresting or inhibiting the growth of bacteria comprising contacting bacteria with a compound according to claim 1 in an amount sufficient to inhibit the growth of said bacteria.

* * * * *